(12) United States Patent
Falco et al.

(10) Patent No.: US 8,366,618 B2
(45) Date of Patent: *Feb. 5, 2013

(54) RADIOTHERAPY TREATMENT MONITORING USING ULTRASOUND

(75) Inventors: Tony Falco, La Prairie (CA); Martin Lachaine, Montreal (CA)

(73) Assignee: Elekta Ltd., Montreal, Quebec (CA)

( * ) Notice: Subject to any disclaimer, the term of this patent is extended or adjusted under 35 U.S.C. 154(b) by 8 days.

This patent is subject to a terminal disclaimer.

(21) Appl. No.: 12/647,852

(22) Filed: Dec. 28, 2009

(65) Prior Publication Data
US 2010/0099989 A1    Apr. 22, 2010

Related U.S. Application Data

(63) Continuation of application No. 11/230,920, filed on Sep. 20, 2005, now Pat. No. 7,662,097.

(60) Provisional application No. 60/611,361, filed on Sep. 20, 2004.

(51) Int. Cl.
*A61B 8/00* (2006.01)

(52) U.S. Cl. ......................................... 600/437; 600/443

(58) Field of Classification Search .................. 600/439, 600/436; 378/65; 601/1–3
See application file for complete search history.

(56) References Cited

U.S. PATENT DOCUMENTS

| | | | |
|---|---|---|---|
| 3,082,322 A | 3/1963 | Koerner et al. |
| 3,777,124 A | 12/1973 | Pavkovich |
| 3,987,281 A | 10/1976 | Hodes |
| 3,991,310 A | 11/1976 | Morrison |
| 4,118,631 A | 10/1978 | Froggatt |
| 4,618,978 A | 10/1986 | Cosman |
| 4,923,459 A | 5/1990 | Nambu |
| 4,943,990 A | 7/1990 | Schar |
| 5,039,867 A | 8/1991 | Nishihara et al. |
| 5,080,100 A | 1/1992 | Trotel |
| 5,099,846 A | 3/1992 | Hardy |
| 5,107,839 A | 4/1992 | Houdek et al. |
| 5,117,829 A | 6/1992 | Miller et al. |
| 5,207,223 A | 5/1993 | Adler |
| 5,222,499 A | 6/1993 | Allen et al. |
| 5,291,889 A | 3/1994 | Kenet et al. |
| 5,295,483 A | 3/1994 | Nowacki et al. |
| 5,301,674 A | 4/1994 | Erikson et al. |
| 5,379,642 A | 1/1995 | Reckwerdt et al. |
| 5,391,139 A | 2/1995 | Edmundson |
| 5,411,026 A | 5/1995 | Carol |

(Continued)

FOREIGN PATENT DOCUMENTS

| | | |
|---|---|---|
| EP | 0647457 A1 | 4/1995 |
| EP | 1304960 A1 | 5/2003 |

(Continued)

OTHER PUBLICATIONS

Besl et al., *A Method for Registration of 3d Shapes*, IEEE Transactions on Pattern Analysis and Machine Intelligence 14(2):239-256 (1992).

(Continued)

*Primary Examiner* — Jaqueline Cheng
(74) *Attorney, Agent, or Firm* — Goodwin Procter LLP

(57) ABSTRACT

Methods and systems for assessing the effects of therapy on a patient include obtaining baseline and treatment ultrasound scans of a treatment area of a patient where the treatment ultrasound scans are taken subsequent to the baseline scan and at various times during a course of radiotherapy treatment sessions. The baseline and treatment ultrasounds are compared, and as a result a damage map representing cell death within the treatment area can be constructed.

27 Claims, 8 Drawing Sheets

Baseline Image Data

Theoretical Tissue Damage

U.S. PATENT DOCUMENTS

| | | | |
|---|---|---|---|
| 5,442,675 | A | 8/1995 | Swerdloff et al. |
| 5,447,154 | A | 9/1995 | Cinquin et al. |
| 5,511,549 | A | 4/1996 | Legg et al. |
| 5,531,227 | A | 7/1996 | Schneider |
| 5,588,432 | A * | 12/1996 | Crowley ............... 600/439 |
| 5,609,485 | A | 3/1997 | Bergman et al. |
| 5,673,300 | A | 9/1997 | Reckwerdt et al. |
| 5,690,108 | A | 11/1997 | Chakeres |
| 5,715,166 | A | 2/1998 | Besl et al. |
| 5,754,623 | A | 5/1998 | Seki |
| 5,810,007 | A | 9/1998 | Holupka et al. |
| 5,991,703 | A | 11/1999 | Kase |
| 6,019,724 | A | 2/2000 | Gronningsaeter et al. |
| 6,106,470 | A | 8/2000 | Geiser et al. |
| 6,117,081 | A | 9/2000 | Jago et al. |
| 6,122,341 | A | 9/2000 | Butler et al. |
| 6,129,670 | A | 10/2000 | Burdette et al. |
| 6,285,805 | B1 | 9/2001 | Gueziec |
| 6,292,578 | B1 | 9/2001 | Kalvin |
| 6,345,114 | B1 | 2/2002 | Mackie et al. |
| 6,359,959 | B1 | 3/2002 | Butler et al. |
| 6,385,286 | B1 | 5/2002 | Fitchard et al. |
| 6,390,982 | B1 | 5/2002 | Bova et al. |
| 6,438,202 | B1 | 8/2002 | Olivera et al. |
| 6,511,430 | B1 * | 1/2003 | Sherar et al. ............... 600/443 |
| 6,516,046 | B1 | 2/2003 | Frohlich et al. |
| 6,535,574 | B1 | 3/2003 | Collins et al. |
| 6,546,073 | B1 | 4/2003 | Lee |
| 6,553,152 | B1 | 4/2003 | Miller et al. |
| 6,560,311 | B1 | 5/2003 | Shepard et al. |
| 6,591,127 | B1 | 7/2003 | McKinnon |
| 6,628,983 | B1 | 9/2003 | Gagnon |
| 6,636,622 | B2 | 10/2003 | Mackie et al. |
| 6,661,870 | B2 | 12/2003 | Kapatoes et al. |
| 6,683,985 | B1 | 1/2004 | Kase et al. |
| 6,755,787 | B2 * | 6/2004 | Hossack et al. ............ 600/447 |
| 2001/0035871 | A1 | 11/2001 | Bieger et al. |
| 2002/0018588 | A1 | 2/2002 | Kusch |
| 2002/0082494 | A1 | 6/2002 | Balloni et al. |
| 2002/0156375 | A1 | 10/2002 | Kessman et al. |
| 2002/0176541 | A1 | 11/2002 | Schubert et al. |
| 2002/0183610 | A1 | 12/2002 | Foley et al. |
| 2002/0188194 | A1 | 12/2002 | Cosman |
| 2003/0018232 | A1 | 1/2003 | Elliott et al. |
| 2003/0112922 | A1 | 6/2003 | Burdette et al. |
| 2005/0215899 | A1 * | 9/2005 | Trahey et al. ............... 600/439 |
| 2007/0167755 | A1 * | 7/2007 | Kolios et al. ............... 600/437 |

FOREIGN PATENT DOCUMENTS

| | | |
|---|---|---|
| FR | 2778574 | 11/1999 |
| WO | WO-9906644 A1 | 2/1999 |
| WO | WO-9926534 A1 | 6/1999 |
| WO | WO-9927839 A2 | 6/1999 |
| WO | WO-0105316 A1 | 1/2001 |
| WO | WO-03076003 A2 | 9/2003 |

OTHER PUBLICATIONS

Booth, *Modelling the impact of treatment uncertainties in radiotherapy*, University of Adelaide, Mar. 2002), Section 2.4 (<http://thesis.library.adelaide.edu.au/uploads/approved/adt-SUA20020816.175301/public/03chapter2.pdf>.

Brujic et al., *Analysis of Free-Form Surface Registration*, International Conference on Image Processing, pp. 393-396 (1996).

Cuisenaire, O., http://www.tele.ucl.ac.be/PEOPLE/OC/these/node74.html, Posted Oct. 5, 1999, Downloaded from the Internet on Aug. 10, 2004.

Cuisenaire, O., http://www.tele.ucl.ac.be/PEOPLE/OC/these/node75.html, Posted Oct. 5, 1999, Downloaded from the Internet on Aug. 10, 2004.

Cuisenaire, O., http://www.tele.ucl.ac.be/PEOPLE/OC/these/node12.html, Posted Oct. 5, 1999, Downloaded from the Internet on Aug. 10, 2004.

Dubois et al. Intraobserver and Interobserver Variability of MR Imaging- and CT-derived Prostate Volumes after Transperineal Interstitial Permanent Prostate Brachytherapy, Radiology. 207(3):785-9 (1998).

Eggert et al., *Simultaneous Registration of Multiple Range Views for Reverse Engineering*, International Conference of Pattern Recognition, pp. 243-247 (1996).

Hanks, et al. , Three Dimensional Conformal External Beam Treatment of Prostate Cancer <http://prostate-help.org/download/pilgrim/10rad.pdf>.

Hanks et al., Clinical and Biochemical Evidence of Control of Prostate Cancer at 5 Years After External Beam Radiation, The Journal of Urology, vol. 154, 456-459 (1995).

Haralick et al., *Pose Estimation From Corresponding Data Point*, IEEE Transactions on Systems, Man, and Cybernetics, 19(6):1426-1446 (1989).

Hua et al., Development of a Semi-Automatic Alignment Tool for Accelerated Localization of the Prostate, Int. J. Radiation Oncology Biol. Phys., 55(3):811-823 (2003).

Jiang et al., *A New Approach to 3-d Registration of Multimodality Medical Images by Surface Matching*, SPIE vol. 1808 Visualization in Biomedical Computing pp. 196-213 (1992).

Krempien et al., Daily patient set-up control in radiation therapy by coded light projection, 3 pages.

Michalski et al., *Three-Dimensional Conformal Radiation Therapy (3DCRT) for Prostate Cancer*, Radiation Oncology Center, Mallinckrodt Institute of Radiology, Washington University Medical Center, St. Louis, Missouri (1996) <http://www.phoenix5.org/Infolink/Michalski/#3>.

Paskalev et al., Daily Target Localization for Prostate Patients based on 3-D Image Correlation, Phys. Med. Biol., vol. 49, pp. 931-939 (2004).

Pennec et al,. A Framework for Uncertainty and Validation of 3-D Registration Methods Based on Points and Frames, International Journal of Computer Vision 25(3), 203-229 (1997).

Pito, *A Registration Aid*, International Conference on Recent Advanced in 3D Digital Imaging and Modelling, pp. 85-92 (1997).

Pollack et al., Conventional vs. Conformal Radiotherapy for Prostate Cancer: Preliminary Results of Dosimetry and Acute Toxicity, Int. J. Radiation Oncology Biol. Phys., 34(3):555-564.

Robb, *Three-Dimensional Visualization in Medicine and Biology*. Book Chapter in: Handbook of Medical Imaging: Processing and Analysis, ed. Isaac N. Bankman, Academic Press, San Diego, CA, Chapter 42, pp. 685-671 (2000).

Robinson, *Advances in Multi-Modal Data Analysis: The ANALYZE Software Environment*, <http://www.ii.metu.edu.tr/~med-ii/makaleler/analyze_sw_enve.pdf>, 5 pages. Downloaded on Aug. 10, 2004.

Soffen E.M. et al. Conformal static field radiation therapy treatment of early prostate cancer versus non-conformal techniques: A reduction in acute morbidity. Int J Radiat Oncol Biol Phys, 24: 485-488 (1992).

Thayananthan, A. et al., <http://mi.eng.cam.ac.uk/~bcirs2/papers/thayananthan_cvpr03,pdf>, pp. 1-8. Downloaded from the Internet on Aug. 10, 2004.

Tome et al., Commissioning and Quality Assurance of an Optically Guided Three-dimensional Ultrasound Target Localization System for Radiotherapy, Med. Phys., 29(8):1781-1788 (2002).

Zhang, Iterative Point Matching for Registration of Free-Form Curves and Surfaces, International Journal of Computer Vision, 13(2):119-152 (1994).

<http://www.ucsf.edu/jpouliot/Course/chapter5.htm>.
<http://www.acmp.org/meetings/hershey_2001/highlights/benedict.pdf>.
<http://www.ucsf.edu/jpouliot/Course/Lesson22.htm>.
<http://www.gemedicalsystems.com/patient/see_treat/positioning.html>.
<http://www.emoryradiationoncology.org/high-technology.htm>.
<http://www.varian.com/pinf/imr000c.html>.
<http://www.ucsf.edu/jpouliot/Course/conformal_radiation_therapy.htm>.

Boctor, et al., A Rapid Calibration Method for Registration and 3D Tracking of Ultrasound Images Using Spatial Localizer, Proceedings of the SPIE (2003).

Claim Chart for Claim 10 of US Patent No. 5,447,154.

Van de Geijn, J. et al. *A Graticule for Evaluation of Megavolt X Ray Port Films*, Radiation Oncology Biology Physics, Nov. 1982, vol. 8, No. 11 pp. 1999-2000.

Bijhold, J. et al. Fast evaluation of patient set-up during radiotherapy by aligning features in portal and simulator images, Phys. Med. Biol., 1999, vol. 36, No. 12, pp. 1665-1679.

Meertens, H. et al. A method for the measurement of field placement errors in digital portal images, Phys. Med. Biol., 1990, vol. 35, No. 3, pp. 299-323.

Aoki, Y. et al. An Integrated Radiotherapy Treatment System and its Clinical Application, Radiation Medicine, vol. 5, No. 4, pp. 131-141, 1987.

Troccaz, J. et al. Conformal external radiotherapy of prostatic carcinoma: requirements and experimental results, Radiotherapy and Oncology 29 (1993) pp. 176-183.

Le Verre, C. et al. Intensity-Based Registration of Portal Images for Patient Positioning in Radiotherapy.

Brunie L. et al. Pre-and intra-irradiation multimodal image registration: principles and first experiments, Radiotherapy and Oncology 29 (1993) pp. 244-252.

Troccaz., J et al. Patient Setup Optimization for External Conformal Radiotherapy, Journal of Image Guided Surgery, 1, pp. 113-120 (1995).

* cited by examiner

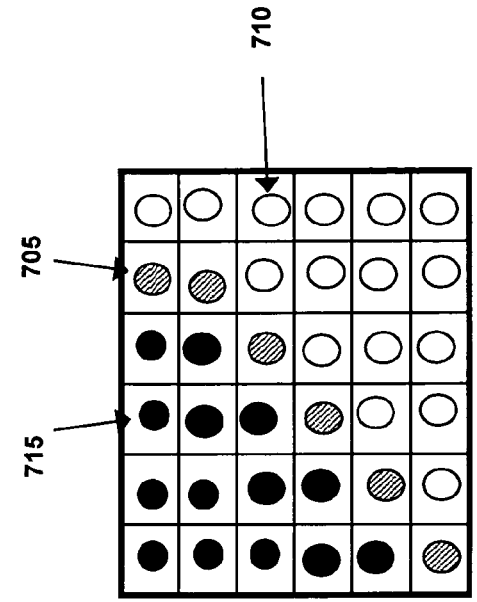
FIG. 7B - Theoretical Tissue Damage
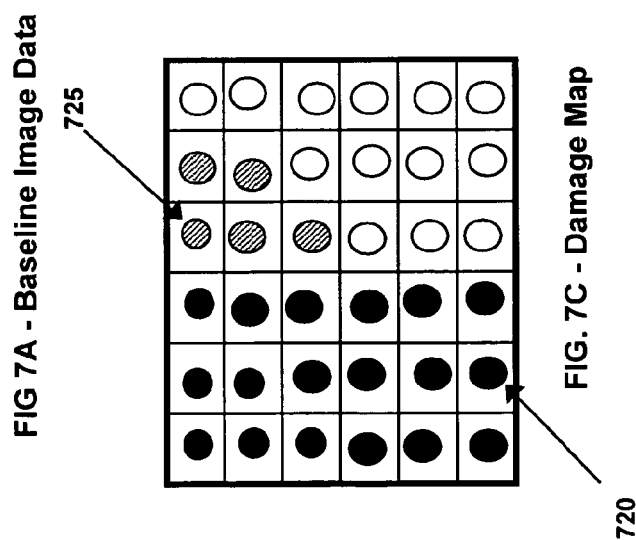
FIG. 7D - Damage Map After Adjustment
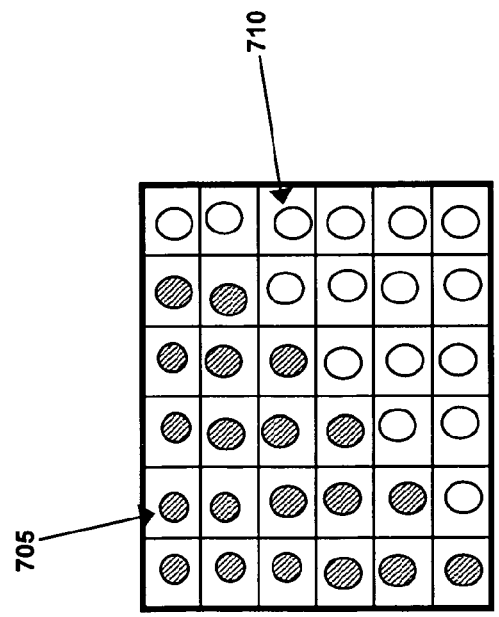
FIG 7A - Baseline Image Data
FIG. 7C - Damage Map

RADIOTHERAPY TREATMENT MONITORING USING ULTRASOUND

CROSS-REFERENCE TO RELATED APPLICATIONS

This application claims priority to U.S. provisional patent application Ser. No. 60/611,361, filed Sep. 20, 2004, the entire disclosure of which is hereby incorporated by reference.

TECHNICAL FIELD

This invention relates to methods and systems for monitoring therapy treatments, and more specifically to observe cell degradation over multiple radiotherapy treatment fractions.

BACKGROUND INFORMATION

In radiotherapy, radiation dosages are typically defined in terms of the energy absorbed per unit mass of tissue. However, relating the prescribed physical dose to the biological effect the radiation will have on the actual tissue being treated is not straightforward. FIG. 1, for example, illustrates these potential dose-response curves 100 indicating the surviving fraction of cells during a treatment protocol versus the administered dose. The dose-response curves can vary among patients, and even at various locations or times for a particular patient. The actual dose-response curve for a particular patient and/or organ, however, is typically not well known in-vivo.

Typically, radiotherapy treatment for deep-seated tumors (as well as to some superficial organs such as the skin) is delivered in a number of fixed sessions, or fractions (e.g., one fraction a day for 30 days) and the dosages are prescribed primarily based on physician and/or institutional experience. For a given total dose, the dose-response curve of a fractional scheme is affected, for example, by the effect of DNA repair and biological damage due to ionizing radiation (or by other therapies such as cryotherapy and chemotherapy). In particular, radiation can directly or indirectly cause breaks in DNA strands, which under some circumstances may be repaired, but in other cases may not be, resulting in cell death.

More particularly, two primary types of cell death occur as a result of radiation exposure—mitotic cell death and apoptosis. In mitotic cell death (which may occur at any time following irradiation), damaged chromosomes cause cells to die as they attempt to divide. Apoptosis, or programmed cell death, occurs normally, and although not typically as prominent as mitotic cell death, can also be induced by radiation and correlate with radiosensitivity.

Because cell death occurs at different rates for different patients, cells, tissues, organs and tumors, dose-response curves for any individual treatment can vary significantly. Therefore, it is difficult to determine, a priori, the proper dose that will kill a given patient's tumor without exposing healthy tissue to unacceptable levels of radiation. Further, the effects of each treatment fraction (both immediately following the fraction and prior to a subsequent fraction) can impact the dose-response curve for a particular treatment. What is needed, therefore, is a way to determine the amount (or lack of) damage caused by therapy dosages, thus giving the physician the ability to determine appropriate adjustments to the therapeutic dosages throughout the treatment cycle that account for the effects of previous radiation fractions on an individual patient's anatomy.

SUMMARY OF THE INVENTION

The invention utilizes ultrasonic tissue characterization techniques as an in-vivo monitoring and/or prediction system of biological damage due to ionizing radiation over the course of a series of radiotherapy fractions, and for follow-up monitoring of the radiation effects. In this way it is possible to determine the effectiveness of a radiotherapy treatment as well as other types of cancer therapy to assist physicians, technicians and radiobiologists in determining if treatment modifications are warranted, as well as a way to document and understand the relationship between dosages and in-vivo damage to cancerous cells and surrounding healthy tissue.

In accordance with the present invention, a series of low-frequency ultrasound (<20 MHz) scans are used to determine a cell survival fraction (or a surrogate quantity therefor) in-vivo, for tumors undergoing radiotherapy. The invention goes beyond measuring physical doses using point dosimeters and exit dosimetry, and unlike high-frequency measurement of apoptosis, measures cell survival over time in three-dimensions—i.e. before, during and after treatment for various sections of the treatment area. Furthermore, by using lower frequencies, the invention can determine changes to cellular size, structure, and/or survival in deep-seated tissues and tumors as well as those closer to the surface. These changes can be viewed over an extended period of time and may be extrapolated into the future, thus assessing the effectiveness of the treatment as (and after) it is delivered (or proposed to be delivered) to the patient.

In one aspect, the present invention provides a method for assessing the effects of treatment on cell condition including the steps of obtaining a baseline ultrasound scan of a treatment area of a patient, and obtaining subsequent, temporally distinct ultrasound scans of the treatment area at various times. The subsequent ("treatment") scans are taken during the course of (or, in some cases, sometime after) various treatment sessions, and the baseline scan and the subsequent scans are compared. The method further includes constructing a damage map (depicting, for example, the spatial distribution and/or progression of cell death) of the treatment area based on the comparison.

In some embodiments, the baseline scans and/or treatment scans can be two- or three-dimensional ultrasound scans. The ultrasound scans can be taken using a low-frequency ultrasound scanner at a frequency below 20 MHz, for example. The treatment sessions can be one or more of radiation treatment, chemotherapy, cryotherapy, and/or brachytherapy. In some cases, the ultrasound treatment scans can be taken following and/or preceding a treatment session. A B-mode scan can be taken prior to the baseline scan (or any of the treatment scans) to determine an anatomical feature of interest within (or near) the treatment area. In some embodiments, the feature may be segmented in the B-mode scan.

Construction of the damage map may include characterizing the power spectrum from the baseline scan, the treatment scans, or both. In some embodiments a damage map constructed from one of the treatment scans can be superimposed with a damage map constructed from the baseline scan (or subsequent treatment scans). A series of damage maps can be constructed using the baseline scan and the treatment scans, and used to build a predictive model that predicts the effects of future radiotherapy sessions on tissue, and to plan subsequent radiotherapy treatment sessions. As one example, the method can include selecting a hypothetical radiation dosage and delivery pattern and, using the predictive model, generate an expected tissue damage map resulting from the dosage and delivery pattern. The comparisons among the baseline scan and the treatment scans can also be used to determine an average damage value for a region.

In another aspect, a system for determining cell condition in response to treatment includes a register for receiving baseline and treatment ultrasound scans of a treatment area, where the treatment ultrasound scans are taken subsequent to the baseline scan and at various times during a course of treatment sessions. The system also includes a comparator module for comparing the baseline ultrasound scan and the treatment ultrasound scans and, based on the comparison, constructing a damage map representing cell death within the treatment area.

In some embodiments, the system includes a display (either static or interactive) for displaying the damage map, and may also include one or more input devices to allow users to adjust treatment parameters, enter data, and/or manipulate the ultrasound scans.

In another aspect, the invention provides software in computer-readable form for performing the methods described herein.

BRIEF DESCRIPTION OF FIGURES

In the drawings, like reference characters generally refer to the same parts throughout the different views. Also, the drawings are not necessarily to scale, emphasis instead generally being placed upon illustrating the principles of the invention.

FIGS. 7A-7D are schematic illustrations of tissue health within a treatment area in accordance with one embodiment of the invention.

DETAILED DESCRIPTION

Throughout the following descriptions and examples, the invention is described in the context of monitoring and measuring the effects of radiotherapy as administered to a cancerous tumor or lesion. However, it is to be understood that the present invention may be applied to monitoring various physical and/or biological attributes of virtually any mass within or on a patient in response to any form of treatment. For example, the therapy can include one or more of radiation, cryotherapy, or any other treatment method that can affect tissue biology at the cellular level.

Typically, B-mode medical ultrasound consists of pressure waves (referred to as RF image data) that are detected by transducers and converted to pixel values by extracting the envelope of the waves. One imaging parameter in ultrasound is the operational frequency. Generally, the higher the frequency, the better the intrinsic resolution of the images produced by the ultrasound system. Because the attenuation of ultrasonic waves increases as the frequency is increased, higher frequencies (e.g., 10 MHz) are typically chosen for imaging of superficial structures, and lower frequencies (e.g., 3 MHz) are used for imaging deep-seated structures. In addition, high-frequency ultrasound imaging uses frequencies above 20 MHz to observe the effects of various treatments at the cellular level.

Figure 1:
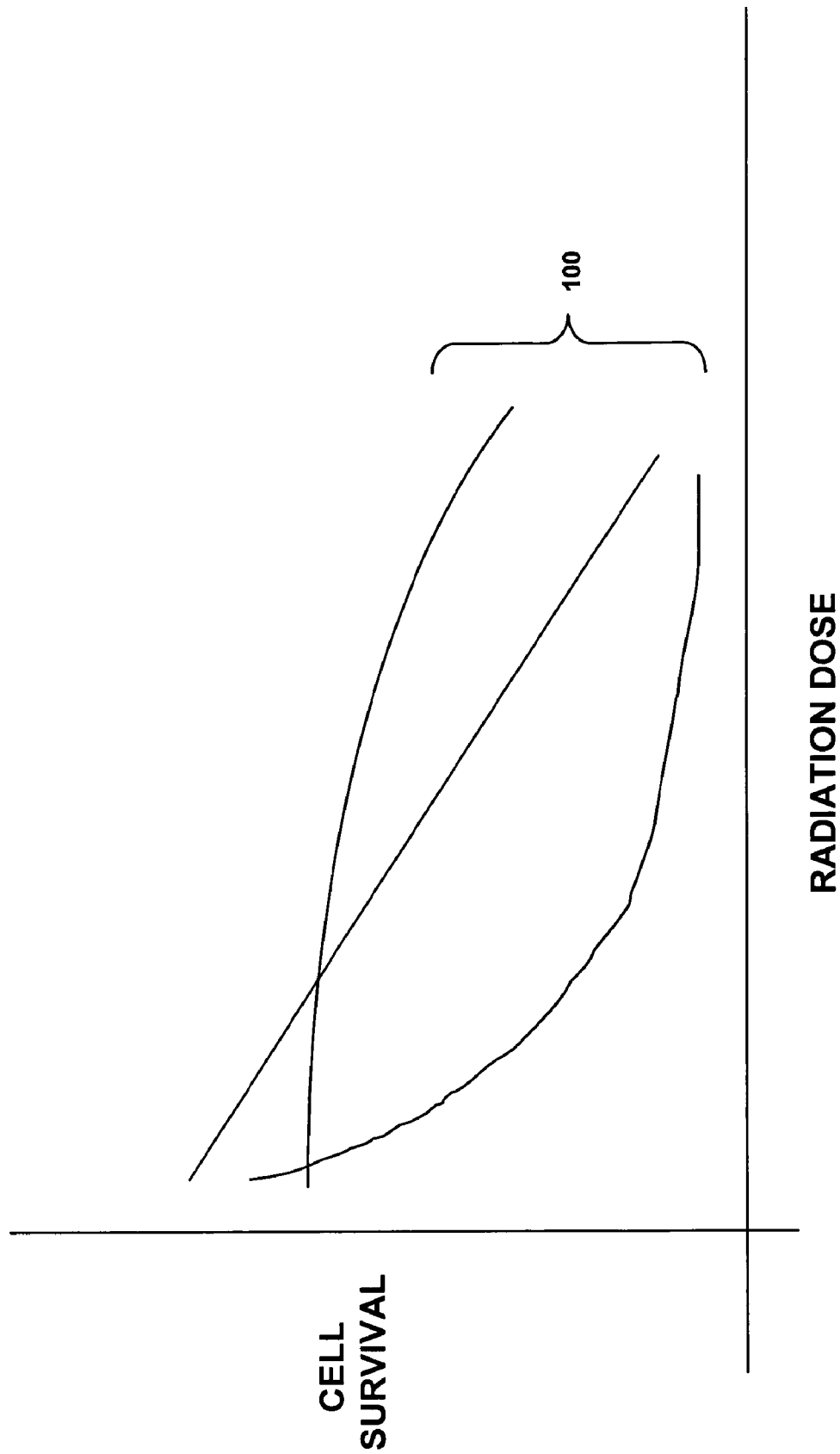
FIG. 1 is a graphical representation of various dose-response curves illustrating the surviving fraction of cells versus radiation dose for different treatments.
Figure 2:
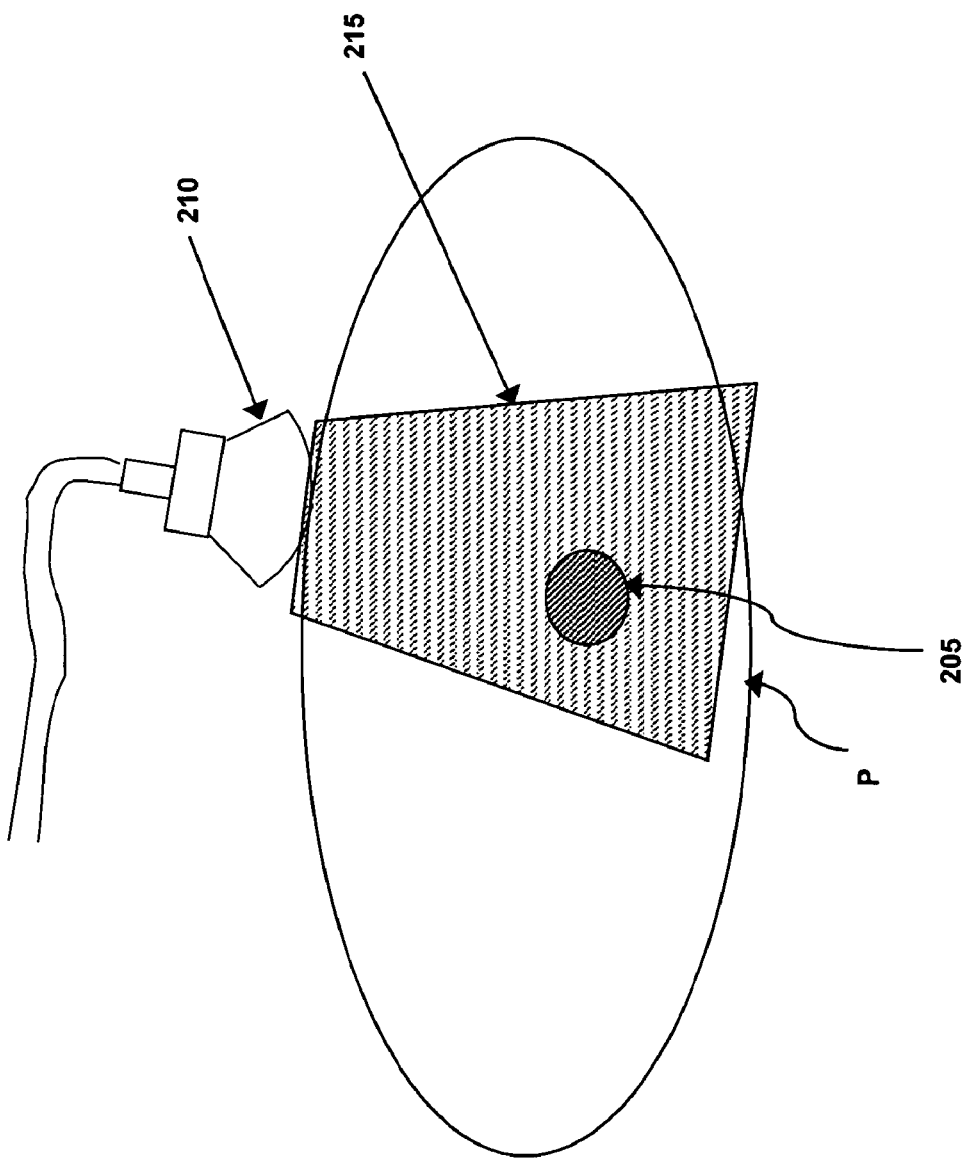
FIG. 2 is a schematic diagram illustrating the use of a hand-held imaging device to obtain data used to construct an initial map of a lesion in accordance with one embodiment of the invention.

Referring to FIG. 2, a series of low-frequency (<20 MHz) ultrasonic RF data scans are acquired at various times before, during and after the course of a patient's radiotherapy treatment, which is typically given in many fractions over an extended period of time. For example, an RF ultrasound scan is taken of a deep-seated tumor 205 within the illustrated region of a patient P prior to administration of the first radiotherapy fraction. The scan can be taken in one, two, or three dimensions to obtain ultrasonic RF data, using, for example, a hand-held ultrasonic scanning device 210. This initial scan 215 is deemed to be the "baseline"—i.e., the planning or preparation scan. At various times throughout the course of radiotherapy treatment, the patient is rescanned in a similar fashion. The subsequent scanning can be done just following the administration of a new radiotherapy fraction, just prior to a fraction, at any point (or points) between fractions, and/or after the last fraction.

In addition to being useful for visualization of a patient's anatomy, there is additional information in the RF image data which can be compared to RF image data from prior scans and/or the baseline, facilitating identification of biological changes among any set of scans (including the baseline scan). These changes can then be used to determine a one-, two-, or three-dimensional map of biological cell damage due to the effects of radiotherapy. Thus, the various ultrasound scans taken over time, when viewed together, act as an in-vivo biological dosimeter, indicating the effective dosage that was delivered to a particular treatment area of the patient (as well as to tissues outside the treatment region) and the resulting tissue damage.

In some embodiments, B-mode ultrasound scans are obtained prior to the initial baseline ultrasound scan to identify the relevant anatomical regions of interest, thus aiding the guidance of the subsequent ultrasound. Further, the B-mode scans may be used to enhance the visual display of the damage map by overlaying the B-mode scan with the damage map image. The B-mode scan can also be used to facilitate the calculation of various treatment parameters (e.g., average of tissue damage over a given tumor site or organ), and to account for the effect of organ motion and shape changes.

Figure 3:
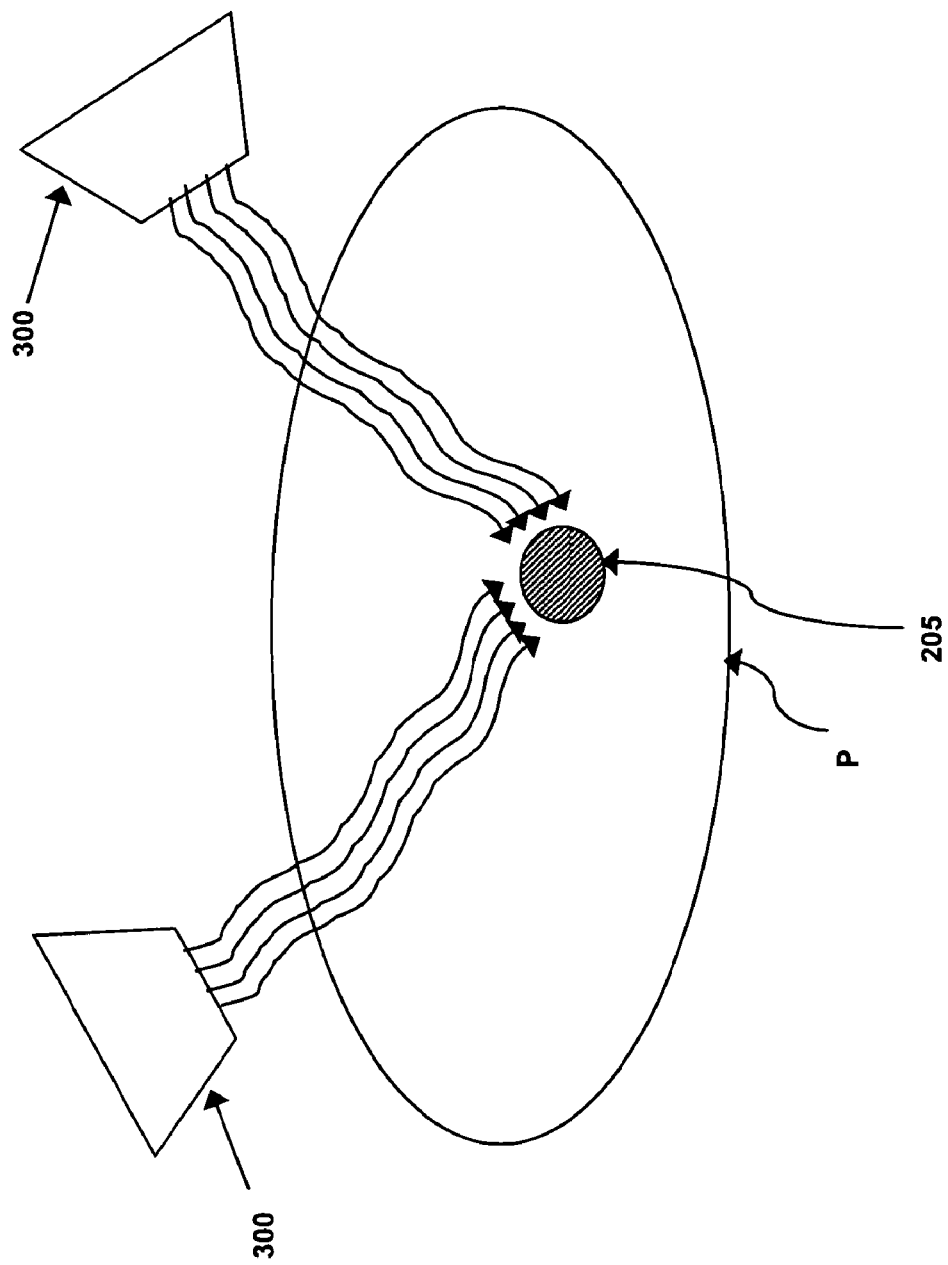
FIG. 3 is a schematic diagram illustrating the delivery of radiotherapy to the lesion of FIG. 2.
Figure 4:
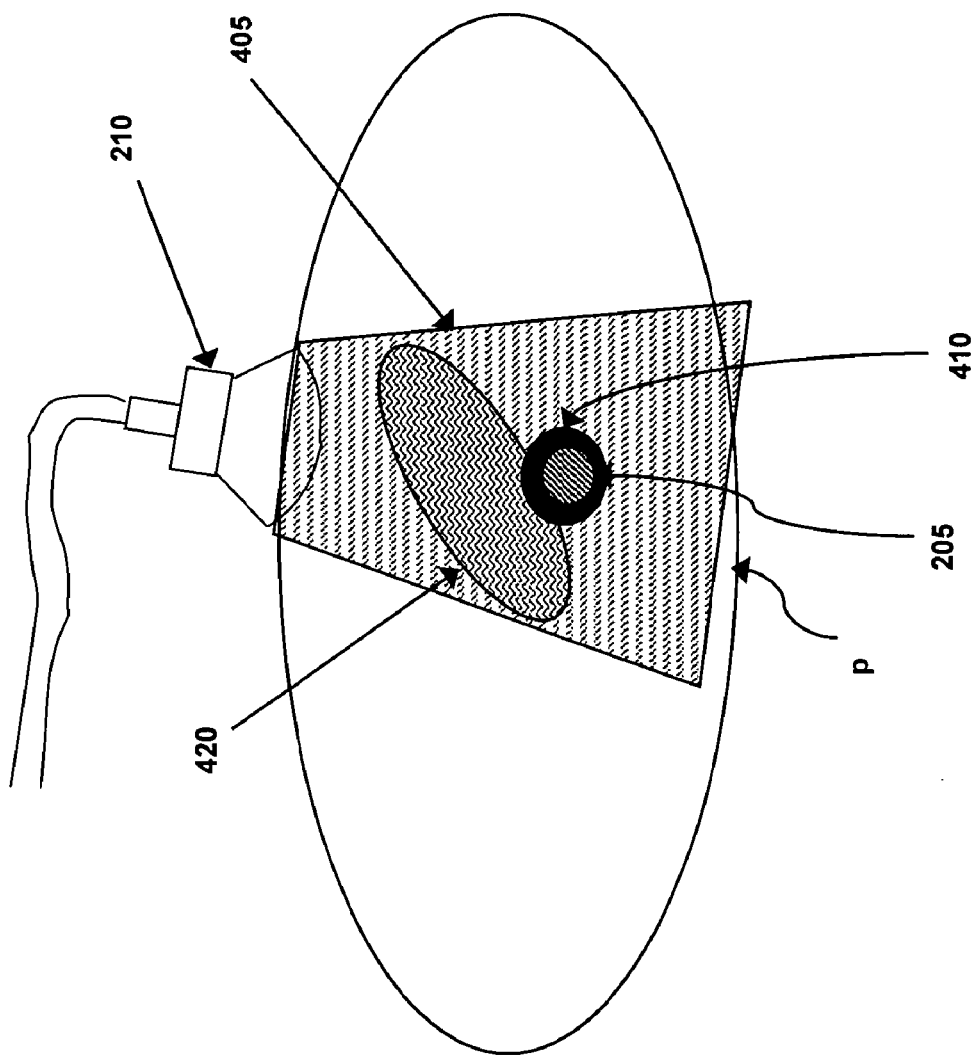
FIG. 4 is a schematic diagram illustrating the use of a hand-held imaging device to obtain data to construct a treatment map of a lesion during the course of radiotherapy in accordance with one embodiment of the invention.

Referring to FIG. 3, sometime after the baseline scan is obtained, the first radiotherapy treatment is administered to the tumor 205 using, for example, an external single-beam conformal radiation device 300 that can be rotated around the patient to administer treatment from various angles. In other embodiments, a multi-beam device may be used. As shown in FIG. 4, immediately following the treatment (or some short time thereafter), a post-radiation ultrasound scan (a "treatment scan") 405 is acquired. Data from the treatment scan 405 provides an indication of the state of both the remaining tumor cells 205, the dead cells 410 killed by the radiotherapy, as well as one or more anatomical features, such as an organ 420 as imaged using the B-mode scan referenced above. By analyzing the various post-irradiation and baseline RF scan parameters, a biological damage map can be constructed, which in turn may be used by the physician to determine the effectiveness of the treatment (and the extent of unwanted damage to healthy tissue) throughout the region of interest (or at particular points of interest) and possibly to alter the treatment plan accordingly.

Because cell death is not necessarily manifested immediately after a treatment session (it may take hours, days or even months), the various RF scans can be obtained at any time before, during and after the course of treatment, such as prior to and/or after each treatment session. In addition to a full map of biological damage, an average measure of biological damage over a region of interest, such as a segmented structure or lesion, can also be calculated and plotted over time throughout and after treatment, thereby providing the physician an indication of treatment efficacy for specific regions within the treatment area.

Figure 5:
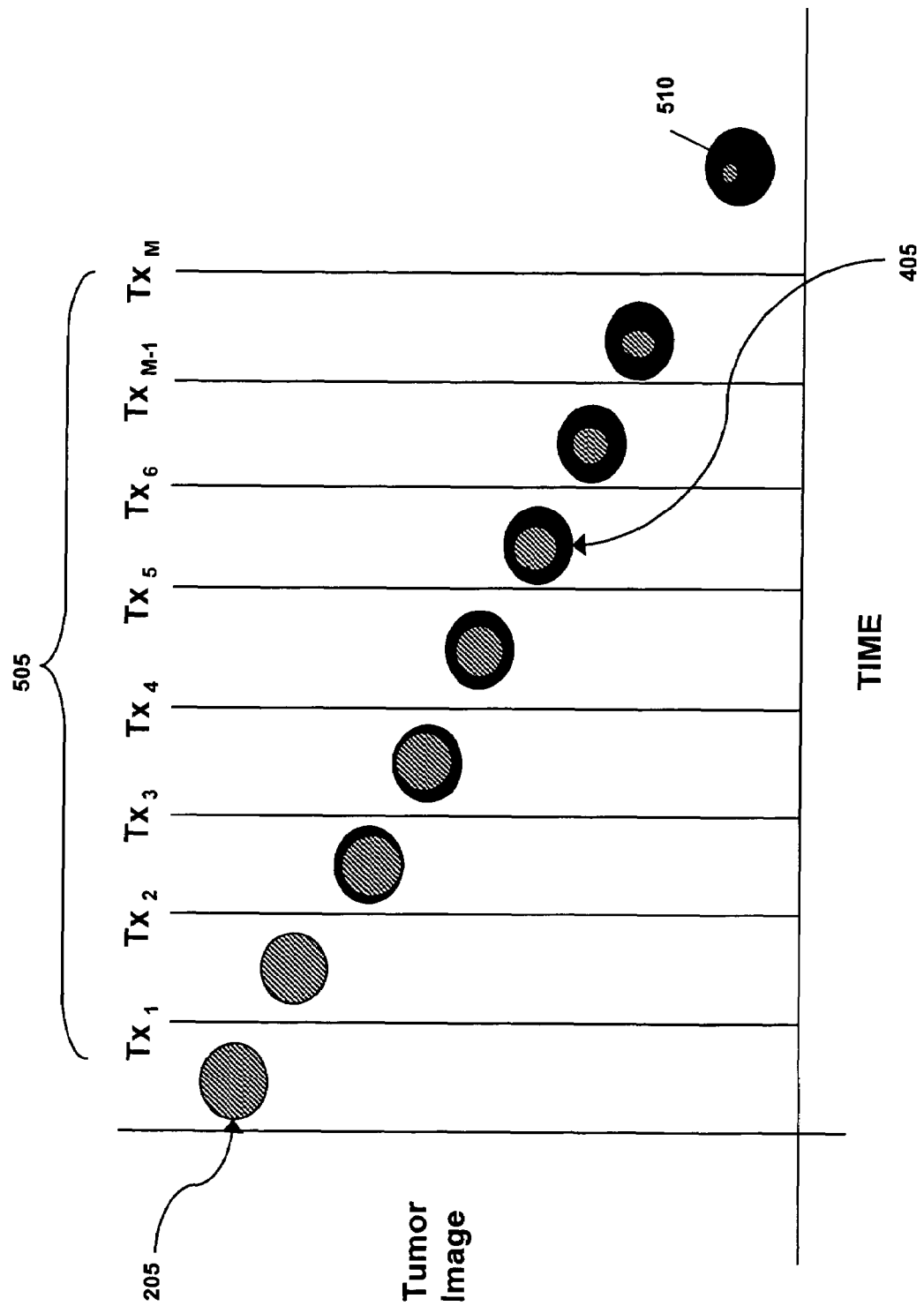
FIG. 5 is a graphical representation of the average biological damage in a region of interest before, during and after being subjected to one or more radiation treatments.

Referring to FIG. 5, for example, tumor 205 is depicted as it appears in the baseline scan, with a high degree of cell survival prior to the administration of the first radiotherapy treatment. A series of treatment fractions 505 ($Tx_1$ through $Tx_m$) is delivered, and at one or more times between the fractions the treatment ultrasounds are obtained showing non-uniform, non-linear tissue damage over time, with portions of the tumor remaining untreated, and other portions 405 having been irradiated. In other cases, portions of the tumor may have received treatment, but due to one or more factors (e.g., radioresistancy) the treatment may not have been effective to kill the cancerous cells. This data can be plotted throughout treatment to ensure the radiotherapy is killing the intended cells. In some instances, a scan 510 can be obtained subsequent to the last fraction to determine the full effects of the treatment, which may not be apparent for weeks, or even months after treatment.

As a result, the RF image data from ultrasound scans taken with each successive treatment can be used to construct a model describing the extent to which tissue damage is accumulating (or not accumulating), and in some cases, at what regions within the treatment area (or along which directions) it is accumulating more than others. The model provides both a spatial and time-based view of how the radiotherapy is affecting that particular patient's cells at various locations within the treatment area due to the cumulative effects of the dosages over time, and the variations in tissue densities and sensitivities at various locations within the treatment area. The model may then be used to generate a predicted map of tissue response to the next proposed treatment or series of treatments, thus allowing a physician to alter the treatment plan if the predicted tissue response is not consistent with the treatment goals, or somehow varies from the theoretical response assumed during the treatment planning stage. Further, a physician may specify different doses and exposure areas for subsequent treatments, and, using the model, obtain a predicted tissue damage map for each hypothetical treatment, using the results to select the most appropriate treatment parameters.

Figure 6:
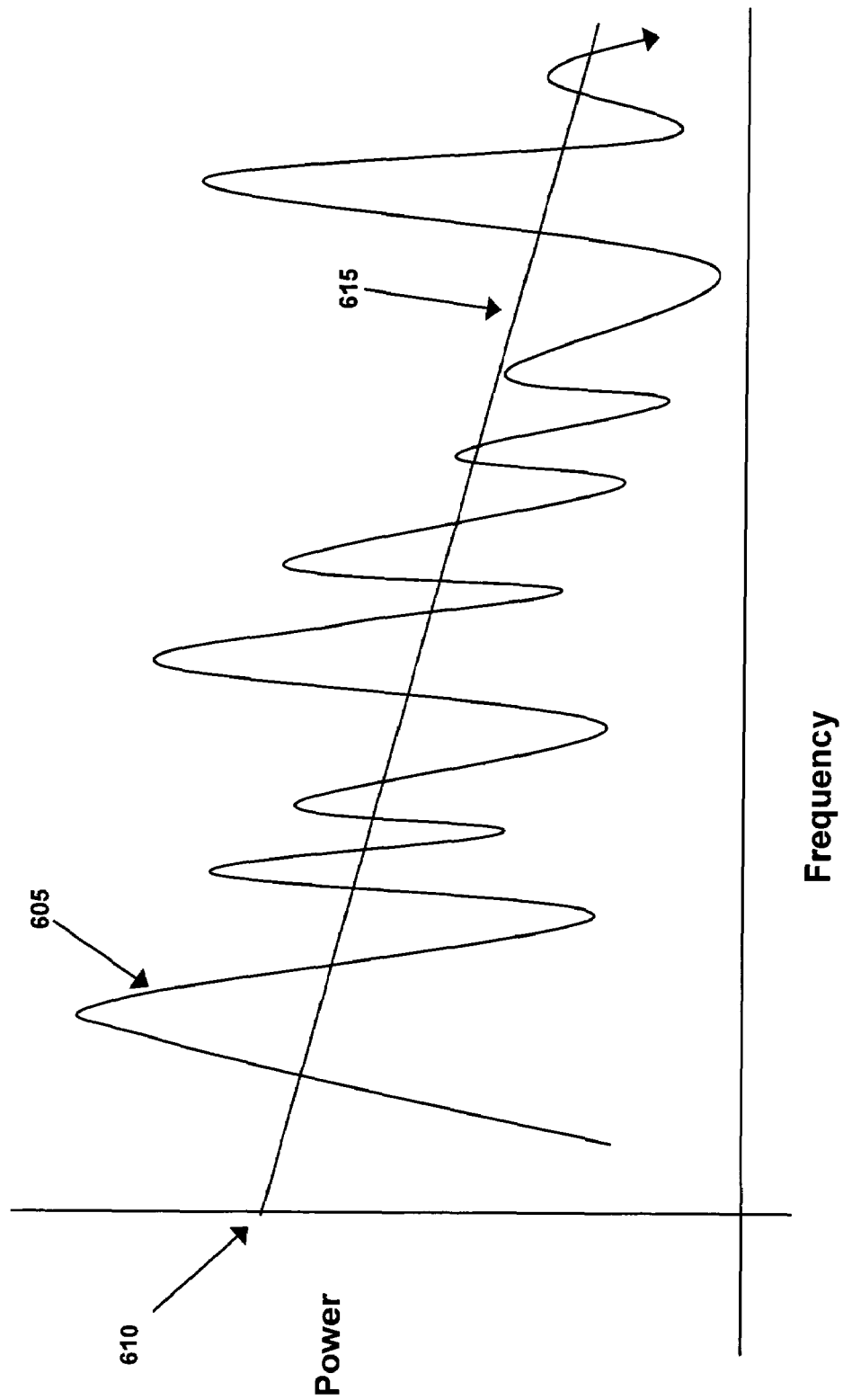
FIG. 6 is a graphical representation of the power spectrum calculated from data acquired in accordance with one embodiment of the invention.

More specifically, one way of determining a damage map from the RF scans includes characterizing the power spectrum for the regions of interest surrounding each pixel or voxel representing the ultrasound scan. For example and with reference to FIG. 6, the RF image data expressed as a signal amplitude over space is transformed (using, e.g., a Fourier transform) into a power spectrum 605 showing the signal's power as a function of frequency. Other techniques for calculating the power spectrum, such as the maximum entropy method, may also be used. The power spectrum may be calculated over a larger region, such as the entire treatment volume, a portion of the treatment volume, or an organ or a lesion of interest in order to obtain a "regional" damage value. In some cases, the damage map can be calculated for particular pixel or voxel by calculating the power spectrum for an area including the pixel or voxel of interest and those adjacent to it. In some embodiments, a known reference material (e.g., glass) is used to obtain a calibrated power spectrum, and the subsequent spectra may then be normalized using the calibrated spectrum.

To relate the power spectrum 605 to tissue damage and/or health, various analytical parameters such as the intercept 610, slope and midband fit 615 of the power spectrum can be extracted from the RF image data, and these parameters in turn can be used to derive the acoustic concentration of scatterers, $CQ^2$, where C is the concentration of scatterers (an indication of the surviving fraction of cells) and Q is the relative impedance of the scatterers. (See, for example, Lizzi F. L., Astor M., Liu T., Deng C., Coleman D. J., Silverman R. H., "Ultrasonic Spectrum Analysis for Tissue Assays and Therapy Evaluation" Int. J. Imaging Syst. Technol. 8, 3-10, 1997). In some cases, C can be isolated and used as a direct representation of cell survival and tissue health, but, in cases where C cannot be isolated and where $Q^2$ remains relatively constant over time for a particular frequency, $CQ^2$ can be used as a surrogate for C, and thus as an adequate representation of tissue health. The difference in C and/or $CQ^2$ (or related quantities) over time and/or at different points within or around the treatment area gives an indication of the surviving fraction of cells during the course of radiotherapy at various points in space. These differences can, in some embodiments, be built up from smaller regions within and/or around the treatment area to produce a tissue damage map of the entire treatment area, thus relating treatment dosages to variations in tissue health in two- or three-dimensions for a particular anatomical area of a particular patient, at a particular time. A model relating tissue damage to dosage and time is obtained from the individual, time-specific damage maps using conventional curve-fitting or interpolation techniques. Using this model, physicians can then predict the effect of a particular dose (or series of doses) at a particular time for a specific anatomical area of an individual patient.

Analysis of the RF image data can involve such analytical quantities as the power spectrum, autocorrelation function (i.e., the correlation of the RF signal with itself), and attenuation estimates, but can also or instead include other quantities. These quantities represent various ways of detecting relative changes in tissue makeup from RF image data, and can either be averaged in a region of interest or displayed in full. Alternatively or in addition, parameters such as the slope of the power spectrum can be extracted from these quantities. Instead of or in addition to a region-of-interest average, the spatial variation of these parameters can be displayed and analyzed in three dimensions. As one goal of the invention is to describe changes in the parameters over the course of treatment to determine tissue damage, a difference, ratio, or other mathematical operation between sets of images and/or sets of parameters can also be calculated, and the results may change the physician's treatment decisions regarding length of treatment or treatment modality. In some cases, the quantities may be followed over the entire course of treatment, whereas in other embodiments, over some fraction of the treatment regimen.

FIGS. 7A-7D illustrate one possible way the damage map described above may be used to adjust treatment parameters in response to non-uniform or unforeseen cell damage during the course of a series of radiotherapy treatment fractions. An initial baseline image (FIG. 7A) illustrates two groupings of cells, cancerous cells 705 (shaded) and healthy cells 710

(unshaded). Using the baseline image as a guide, the physician determines a treatment course, using the theoretical tissue damage progression (FIG. 7B). The theoretical damage progression may include one or more assumptions regarding absorption, density, sensitivity etc. and therefore indicates that the radiotherapy will kill off cells starting in the upper left, and move diagonally downward and to the right across the map, resulting in dead cells 715, to-be-treated cancerous cells 705, and the remaining healthy cells 710. Using the techniques described above, however, the resulting damage map (FIG. 7C) obtained from a treatment ultrasound image indicates quite a different result. Instead of progressing as intended, the radiotherapy has affected previously healthy cells 720 and had no effect on cancerous cells 725. Noting this deviation from the theoretical damage map (FIG. 7B), the physician can adjust various treatment parameters such as beam angles, dosages and patient position mid-treatment. As a result, the post-adjustment damage map (FIG. 7D) indicates that the previously unaffected cancerous cells 730 are now killed off, and cell damage has not progressed at the boundary 735 of healthy cells and dead cells. As mentioned above, this two-dimensional modeling can be extended to three dimensions using three-dimensional ultrasound imaging techniques.

In some instances, determination of tissue-specific properties from ultrasound RF image data can be affected by transducer-dependent effects, which are generally not desirable. One way to compensate for these effects is to utilize a "phantom" to calibrate the imaging device and normalizing data received during normal usage to data acquired using the phantom. Alternatively, data can be normalized to either the baseline scan or an earlier scan of the particular patient, thus creating a patient-specific calibration, which in some cases may be more accurate than a phantom-based calibration.

One variation of the invention includes acquiring one or more three-dimensional freehand B-mode ultrasound scans prior to the RF data scans (or each such scan, if desired) and segmenting (i.e., partitioning into discrete volumes) the anatomy of interest at each treatment stage from the B-mode scan. Such an approach provides anatomical guidance for the subsequent RF scans, and also facilitates the analysis of the RF data in anatomical regions of interest that may change shape and position over time. For example, the B-mode images of a prostate gland being treated for cancer can be segmented both before and after treatment delivery, and RF data analysis parameters can subsequently be averaged within each prostate volume. Alternatively, the map of biological damage can be superimposed on the B-mode anatomical scan for visualization.

The technique is not only applicable to radiation therapy but to any other therapy which leads to tissue damage, e.g., the immediate or eventual killing of cells. Such therapies can include, for example, chemotherapy, cryotherapy, single-fraction radiosurgery, hyperthermia, or brachytherapy, or any combination of these treatment methods. Comparison of the set of scans to the baseline scan provides a direct measurement of the effectiveness of the treatment in both time and space, allowing the physician to adapt the treatment based on the results.

Figure 8:
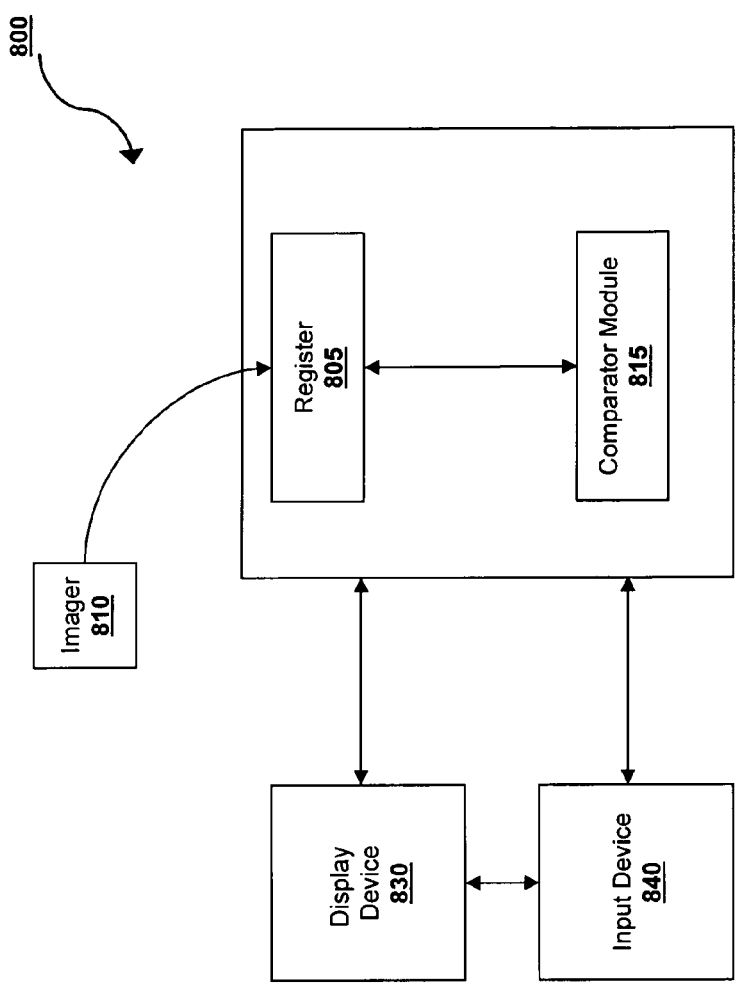
FIG. 8 is a schematic illustration of a biological damage monitoring system according to an embodiment of the invention.

Referring to FIG. 8, one embodiment of a system 800 for performing the techniques described above includes a register 805 or other volatile or non-volatile storage device that receives image data from an imaging device 810 (such as a hand-held ultrasound device) via a cord or wire, or in some embodiments via wireless communications. The system also includes a comparator module 815 that, based on the image data, uses the techniques described above to construct a damage map of the treatment area. In some embodiments, the system also includes a display 830 and an associated user interface (not shown) allowing a user to view and manipulate the ultrasound images and/or damage maps. The display 830 and user interface can be provided as one integral unit or separate units (as shown) and may also include one or more user input devices 840 such as a keyboard and/or mouse. The display 830 can be passive (e.g., a "dumb" CRT or LCD screen) or in some cases interactive, facilitating direct user interaction with the images and models through touch-screens (using, for example, the physician's finger as an input device) and/or various other input devices such as a stylus, light pen, or pointer. The display 830 and input devices 840 may be located in a different location that the register 805 and/or comparator 815, thus allowing users to receive, view, and manipulate images in remote locations using, for example, wireless devices, handheld personal data assistants, notebook computers, among others.

In various embodiments the register 805 and/or comparator module 815 may be provided as either software, hardware, or some combination thereof. For example, the system may be implemented on one or more server-class computers, such as a PC having a CPU board containing one or more processors such as the Pentium or Celeron family of processors manufactured by Intel Corporation of Santa Clara, Calif., the 680x0 and POWER PC family of processors manufactured by Motorola Corporation of Schaumburg, Ill., and/or the ATHLON line of processors manufactured by Advanced Micro Devices, Inc., of Sunnyvale, Calif. The processor may also include a main memory unit for storing programs and/or data relating to the methods described above. The memory may include random access memory (RAM), read only memory (ROM), and/or FLASH memory residing on commonly available hardware such as one or more application specific integrated circuits (ASIC), field programmable gate arrays (FPGA), electrically erasable programmable read-only memories (EEPROM), programmable read-only memories (PROM), programmable logic devices (PLD), or read-only memory devices (ROM). In some embodiments, the programs may be provided using external RAM and/or ROM such as optical disks, magnetic disks, as well as other commonly storage devices.

For embodiments in which the invention is provided as a software program, the program may be written in any one of a number of high level languages such as FORTRAN, PASCAL, JAVA, C, C++, C#, LISP, PERL, BASIC or any suitable programming language. Additionally, the software can be implemented in an assembly language and/or machine language directed to the microprocessor resident on a target device.

It will therefore be seen that the foregoing represents an improved method and supporting system for monitoring the biological effects of radiotherapy over the course of a treatment regimen. The terms and expressions employed herein are used as terms of description and not of limitation, and there is no intention, in the use of such terms and expressions, of excluding any equivalents of the features shown and described or portions thereof, but it is recognized that various modifications are possible within the scope of the invention claimed. Moreover, although the above-listed text and drawings contain titles headings, it is to be understood that these title and headings do not, and are not intended to limit the present invention, but rather, they serve merely as titles and headings of convenience.

The invention claimed is:

1. A method of assessing cell condition in response to treatment, the method comprising the steps of:

a. obtaining a baseline ultrasound scan of a treatment area of a patient;
b. obtaining, subsequent to the baseline scan, one or more temporally distinct treatment ultrasound scans of the treatment area at various times during a course of treatment sessions;
c. comparing at least one of the one or more treatment ultrasound scans to the baseline ultrasound scan; and
d. based on the comparison, assessing cell condition in the treatment area in response to the treatment sessions, wherein the baseline ultrasound scan and the one or more treatment ultrasound scans are taken at a frequency below 20 MHz.

2. The method of claim 1 wherein the baseline ultrasound scan is rendered in two dimensions.

3. The method of claim 1 wherein the one or more treatment ultrasound scans are rendered in two dimensions.

4. The method of claim 1 wherein the baseline ultrasound scan is rendered in three dimensions.

5. The method of claim 1 wherein the one or more treatment ultrasound scans are rendered in three dimensions.

6. The method of claim 1 wherein the treatment sessions include one or more sessions of radiation treatment, chemotherapy, cryotherapy, and brachytherapy.

7. The method of claim 1 wherein each of the one or more treatment ultrasound scans are obtained substantially just following one of the treatment sessions.

8. The method of claim 1 wherein each of the one or more treatment ultrasound scans is obtained substantially just prior to treatment delivery.

9. The method of claim 1 further comprising obtaining, prior to obtaining the baseline ultrasound scan, a B-mode scan to determine an anatomical feature of interest within the treatment area.

10. The method of claim 9 further comprising creating a segmented representation of the anatomical feature of interest using the B-mode scan.

11. The method of claim 1 further comprising obtaining, prior to obtaining the one or more treatment ultrasound scans, a B-mode scan to determine an anatomical feature of interest within the treatment area.

12. The method of claim 1 wherein assessing cell condition in the treatment area comprises characterizing a power spectrum from one or more of the baseline scan and the treatment scans.

13. The method of claim 12 wherein the power spectrum is characterized by estimating an acoustic concentration of scatters in one or more of the baseline scan and the treatment scans.

14. The method of claim 1 further comprising using the results of the comparison to plan a subsequent treatment session.

15. The method of claim 1 wherein assessing cell condition in the treatment area comprises determining an average cell condition value over a region of interest.

16. The method of claim 1 wherein assessing cell condition in the treatment area comprises constructing one or more damage maps representing cell damage within the treatment area.

17. The method of claim 16, further comprising superimposing the one or more damage maps with the baseline ultrasound scan.

18. The method of claim 1 wherein the baseline ultrasound scan and the one or more treatment ultrasound scans are taken at a frequency below about 10 MHz.

19. The method of claim 1 wherein the baseline ultrasound scan and the one or more treatment ultrasound scans are taken at a frequency of about 3 MHz.

20. The method of claim 1 wherein assessing cell condition comprises assessing cell death.

21. A system for determining cell condition in response to treatment, the system comprising:
a storage unit configured to receive ultrasound scans of a treatment area, the ultrasound scans comprising:
a baseline ultrasound scan; and
one or more temporally distinct treatment ultrasound scans of the treatment area taken subsequent to the baseline scan and at various times during a course of treatment sessions, wherein the baseline ultrasound scan and the one or more treatment ultrasound scans are taken at a frequency below 20 MHz; and
a comparator module configured to:
(i) compare the baseline ultrasound scan and at least one of the one or more treatment ultrasound scans, and
(ii) based on the comparison, determine cell condition in the treatment area in response to the treatment sessions.

22. The system of claim 21 wherein the comparator module is configured to construct a plurality of damage maps representing cell condition within the treatment area, the system further comprising a display for displaying one or more of the damage maps.

23. The system of claim 21 further comprising an ultrasound scanning device for obtaining the baseline ultrasound scan and the one or more temporally distinct treatment ultrasound scans.

24. The system of claim 21 further comprising an input device for facilitating one or more of manipulating the ultrasound images, adjusting treatment parameters, and entering analysis data.

25. A non-transitory computer readable medium having computer-readable programs embodied thereon for determining cell condition in response to treatment, the medium comprising computer-readable instructions for:
a. obtaining a plurality of temporally distinct ultrasound scans of a treatment area at various times during a course of treatment sessions, wherein the plurality of ultrasound scans are taken at a frequency below 20 MHz;
b. comparing the plurality of ultrasound scans; and
c. based on the comparison, determining cell condition in the treatment area in response to the treatment sessions.

26. The non-transitory computer readable medium of claim 25 wherein the computer-readable programs further comprise computer-readable instructions for characterizing a power spectrum from one or more of the plurality of ultrasound scans.

27. The non-transitory computer readable medium of claim 25 wherein the computer-readable programs further comprise computer-readable instructions for constructing a series of damage maps representing cell condition within the treatment area.

* * * * *